United States Patent
De Munck

(10) Patent No.: US 9,481,628 B2
(45) Date of Patent: Nov. 1, 2016

(54) ESTERIFICATION PROCESS

(71) Applicant: ExxonMobil Chemical Patents Inc., Baytown, TX (US)

(72) Inventor: Nicholaas A. De Munck, JL Barendrecht (NL)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/385,880

(22) PCT Filed: Mar. 8, 2013

(86) PCT No.: PCT/EP2013/054699
§ 371 (c)(1),
(2) Date: Sep. 17, 2014

(87) PCT Pub. No.: WO2013/143824
PCT Pub. Date: Oct. 3, 2013

(65) Prior Publication Data
US 2015/0051420 A1 Feb. 19, 2015

Related U.S. Application Data

(60) Provisional application No. 61/618,078, filed on Mar. 30, 2012.

(30) Foreign Application Priority Data

May 8, 2012 (EP) .................................... 12167059

(51) Int. Cl.
*C07C 67/08* (2006.01)
*C07C 67/03* (2006.01)
*C07C 67/54* (2006.01)

(52) U.S. Cl.
CPC .............. *C07C 67/03* (2013.01); *C07C 67/54* (2013.01); *Y02P 20/582* (2015.11)

(58) Field of Classification Search
CPC ....... C07C 67/03; C07C 67/54; C07C 69/82; G11C 29/027; G11C 29/18; G11C 29/787; Y02P 20/582

See application file for complete search history.

(56) References Cited

U.S. PATENT DOCUMENTS

| | | | | |
|---|---|---|---|---|
| 3,676,485 A | * | 7/1972 | Lewis | ...................... B01D 1/12 202/197 |
| 7,361,779 B1 | * | 4/2008 | Holt | ........................ C07C 69/82 560/76 |
| 7,964,658 B2 | | 6/2011 | Grass | |
| 2007/0161815 A1 | | 7/2007 | Osborne et al. | |
| 2007/0179229 A1 | * | 8/2007 | Grass | .................... C07C 29/141 524/287 |
| 2008/0183012 A1 | | 7/2008 | Cook et al. | |

FOREIGN PATENT DOCUMENTS

| | | | |
|---|---|---|---|
| JP | 2003-238479 | | 8/2003 |
| JP | 238479 | * | 8/2003 |
| JP | 2006-273799 | | 10/2006 |
| JP | 44-70391 | | 6/2010 |
| WO | WO 2007/021475 | | 2/2007 |
| WO | WO 2008/140177 | | 11/2008 |
| WO | WO 2010/044638 | | 4/2010 |
| WO | WO 2010/071717 | | 6/2010 |
| WO | WO2011161037 | * | 6/2011 |
| WO | WO 2011/161037 | | 12/2011 |

OTHER PUBLICATIONS

Buck, (Efficiency of Fractional Distillation Columns, Ournal of Chemical E Ducation, pp. 475-476 and 492, 1944).*

Firdovsi et al., "Transesterification Reaction of Dimethyl Terephthalate by 2-Ethylhexanol in the Presence of Heterogeneous Catalysts Under Solvent-Free Condition," Chinese Journal of Chemistry, vol. 25, No. 2, Jan. 1, 2007, pp. 246-249.

* cited by examiner

*Primary Examiner* — Yevegeny Valenrod
*Assistant Examiner* — Blaine G Doletski
(74) *Attorney, Agent, or Firm* — Darryl M. Tyus

(57) ABSTRACT

Embodiments of an invention disclosed herein relate to methods to produce terephthalate esters, the methods include esterifying at least one $C_6$-$C_{13}$ alcohol with dimethyl terephthalate (DMT) in the presence of a catalyst to produce the terephthalate esters.

18 Claims, 1 Drawing Sheet

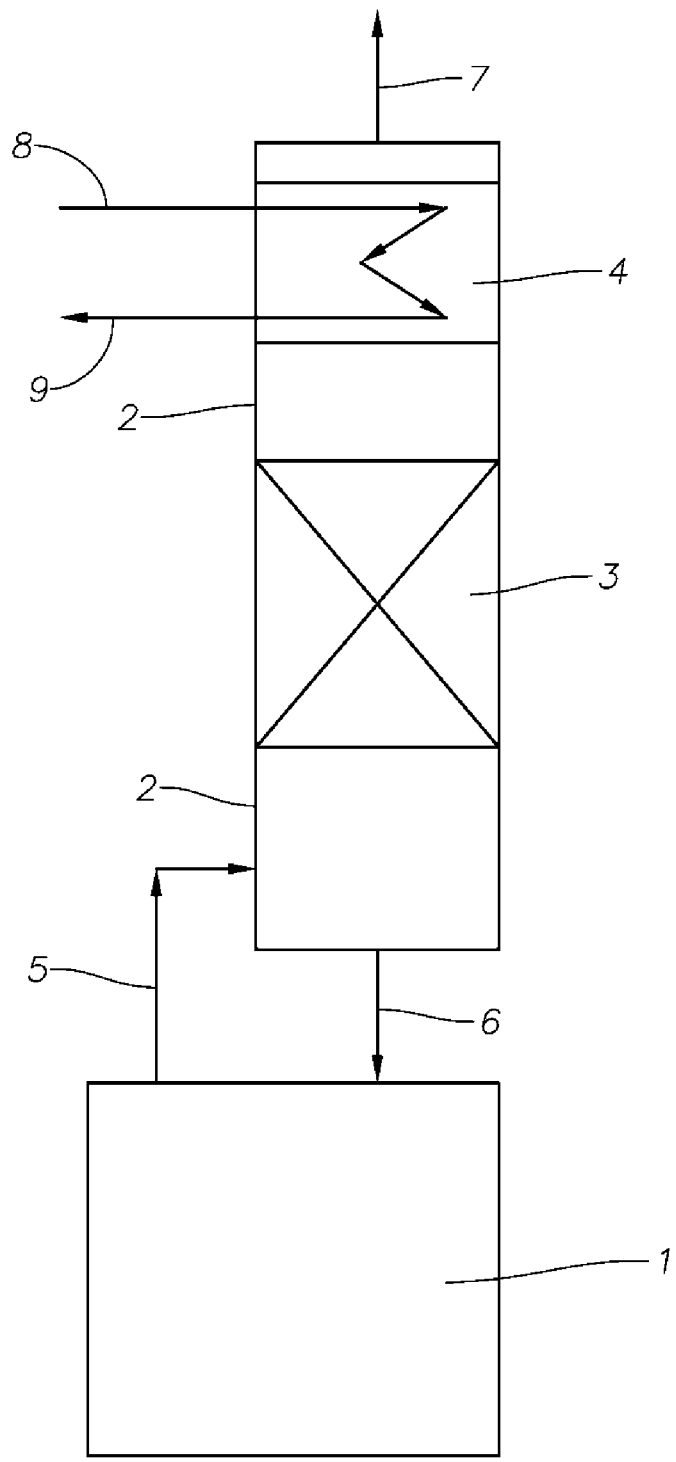

ESTERIFICATION PROCESS

CROSS REFERENCE TO RELATED APPLICATIONS

This application is a national stage application under 35 USC 371 of International Application No. PCT/EP2013/054699, filed Mar. 8, 2013, which claims the benefit of U.S. Provisional Application Ser. No. 61/618,078, filed Mar. 30, 2012, the disclosures of which are fully incorporated herein by reference in their entireties.

FIELD OF THE INVENTION

The present invention relates to the production of terephthalate esters. In particular, embodiments disclosed herein relate to methods to produce terephthalate esters through the esterification of two or more of: $C_6$-$C_{13}$ alcohols, for example, isohexyl alcohol, isoheptyl alcohol, 2-ethyl hexanol (2-EH), isononyl alcohol, isodecyl alcohol, and mixtures thereof, with dimethyl terephthalate (DMT), terephthalic acid (TPA), purified terephthalic acid (PTA), and mixtures thereof, to produce the terephthalate esters.

BACKGROUND

Plasticizers are added to a resin composition (usually a plastomer or an elastomer) to increase the flexibility, workability, or distensibility of the resin composition. The largest use of plasticizers is in the production of "plasticized" or flexible polyvinyl chloride (PVC) products. Common plasticizers include phthalates, in particular, ortho-phthalates, di-2-ethylhexyl phthalate (DEHP), diisononyl phthalate (DINP), diisodecyl phthalate (DIDP), di-octyl phthalate (DOP), dibutyl phthalate (DBP), diisobutyl phthalate (DIBP), benzylbutyl phthalate (BBP), diisoheptyl phthalate (DIHP), and many others.

Typical uses of plasticized PVC include films, sheets, tubing, coated fabrics, wire and cable insulation, jacketing, toys, flooring materials, such as, vinyl sheet flooring or vinyl floor tiles, adhesives, sealants, inks, and medical products, such as, blood bags and tubing.

Other polymer systems that use plasticizers include polyvinyl butyral, acrylic polymers, poly(vinylidene chloride), nylon, polyolefins, polyurethanes, silicon modified polymers, polysulphides, and certain fluoroplastics. Plasticizers may also be used with rubber (although often these materials fall under the definition of extenders for rubber rather than plasticizers).

Although the major commercial plasticizers for PVC are esters of phthalic acid (or the anhydride), recently, there has been an effort to find alternatives to the use of low molecular weight phthalate esters, particularly, in end uses such as food contact articles, such as, bottle cap liners and sealants, cling films, medical applications, such as, examination gloves, films, blood bags, IV delivery systems, flexible tubing, and toys.

In particular, DOP (DEHP) and shorter alkyl chain length phthalate esters have been restricted in certain applications or are the subject of increased scrutiny due to their classification as substances of very high concern (SVHC) under REACH in Europe. Their use in toys is increasingly restricted in some countries. For example, DOP (DEHP) is a versatile and widely applied plasticizer for PVC in many applications and has been for decades. DEHP together with low molecular weight phthalate plasticizers like DBP, DIBP, BBP are listed on the REACH candidate list and subject to authorization. They cannot be produced or used in Europe after the sunset date of February 2015, unless an authorization is being granted for a specific use. Thus, it must be at least contemplated that alternative plasticizers will be required. For these and most other uses of plasticized polymer systems, high molecular weight phthalates like DINP, DIDP, or DPHP have been substituted successfully for the short alkyl chain phthalate esters but there will be additional requirements to develop alternatives to DEHP in certain applications like medical or food contact. A suitable replacement would be produced from readily available materials and commercial processes and provide at least comparable performance properties.

A commercial process to produce DOP (DEHP) includes batch esterification of phthalic acid with 2-ethyl hexanol (2-EH) in the presence of an organic titanate catalyst. Esters, such as para-phthalates or terephthalates, may also be produced from other starting materials including purified terephthalic acid (PTA), terephthalic acid (TPA), or its dimethyl terephthalate (DMT) derivative. (See, for example, WO 2010/071717). However, only one monomeric ester of terephthalic acid has acquired some significance industrially as a plasticizer for PVC, namely di-2-ethylhexyl terephthalate (DEHTP or DOTP).

WO 2007/021475 is directed to the preparation of di-(2-ethylhexyl) terephthalate from terephthalic acid (TPA). More specifically, it discloses a process for the preparation of di-(2-ethylhexyl) terephthalate by the esterification of TPA with 2-ethylhexanol (2-EH) in the presence of a titanium catalyst at elevated temperature and pressure, and the removal of the water of reaction from the reaction mixture by stripping the reactor contents with an inert gas.

U.S. 2007/0161815 and WO 2008/094396 disclose the esterification of TPA with $C_6$-$C_{10}$ alcohols in a reactor equipped with a fractionation column for water removal from the refluxing 2-EH, in the presence of a titanate catalyst, operating at atmospheric pressure and a temperature of 180° C.-225° C. In an example, the reaction time was 8-9 hr to reach the targeted conversion. U.S. 2008/0183012 discloses a similar process configuration to produce di-n-butyl terephthalates by the esterification of TPA with n-butanol in the presence of an acid catalyst at atmospheric pressure, from 110° C.-220° C. temperature, and utilizing the ester product as a solvent.

WO 2008/140177 discloses the preparation method of terephthalic acid ester compositions by reacting terephthalic acid with mixtures of two different alcohols such as 2-ethylhexanol and isononyl alcohol in the presence of a titanate catalyst. In an example, the reaction is carried out at 220° C. for 9 hr at atmospheric pressure under nitrogen bubbling to reach complete conversion.

JP 2006273799 teaches that the particle size of terephthalic acid should have an average diameter of 50-300 micron when used in the esterification of terephthalic acid with 2-ethylhexanol. In an example, the required power for the mixer in the reaction vessel should be less than 5 kW/m$^3$.

U.S. Pat. No. 7,964,658 is directed to the preparation of $C_4$ and $C_5$ alkyl terephthalates by the trans-esterification of dimethyl terephthalate with $C_4$ or $C_5$ alcohols in the presence of an organo-metallic catalyst. The alcohol feed is stepwise added to maintain at atmospheric pressure a constant reaction temperature of 185° C. and a constant reflux temperature of 65° C. In an example, the reaction is completed in 8-9 hr with 0.3 wt % dimethyl and monomethyl esters left in the product.

U.S. Pat. No. 7,361,779 mixtures of n-butyl and iso-butyl terephthalates are synthesized by the trans-esterification of dimethyl terephthalate with n-butanol and iso-butanol in the presence of a titanium compound catalyst. In an example, the reaction time was 7-11.5 hours at 110° C.-150° C. temperature, atmospheric pressure, with a reflux temperature of 65° C.-70° C., and yielded 1.4-2.0 wt. % monomethyl esters in the product.

JP 2003238479 discloses the production of terephthalates by the trans-esterification of dimethyl terephthalate with a $C_6$-$C_{13}$ monohydric alcohol in a two-step production process. In a first step, the methanol product is removed at a controlled steam temperature below the boiling point of the monohydric alcohol and by using a distillation column or a partial condenser until the methyl ester concentration becomes less than 20-30 wt %. In a second step, the reaction temperature is increased from 198° C. to 220° C. after addition of fresh monohydric alcohol to obtain a product containing less than 1 wt. % mono methyl esters.

Other background references include WO 2010/044638 and JP 04470391.

Despite these past endeavors, there exists a need for alternative plasticizers that are not subject to the same classification and restrictions as the low molecular weight phthalates and are produced from raw materials readily available worldwide in large quantities while offering the same general purpose performance properties, for example, as DEHP in existing end use applications. There further exists a need to produce these materials with improved processes for their production.

SUMMARY

In several classes of embodiments, the invention provides for a method to produce a terephthalate ester, the method comprising: esterifying at least one $C_6$-$C_{13}$ alcohol with dimethyl terephthalate (DMT) in the presence of a catalyst to produce the terephthalate ester and methanol;

wherein the terephthalate ester is recovered and at least a portion of the $C_6$-$C_{13}$ alcohol is recovered by fractionation and the partial condensation of the methanol.

Other various embodiments are disclosed and claimed herein.

BRIEF DESCRIPTION OF THE DRAWINGS

FIG. 1 is a schematic representation of a general, typical layout of reactor overhead system with a fractionation tower and a partial condenser.

DETAILED DESCRIPTION

In a class of embodiments, the invention is directed to a method to produce a terephthalate ester, for example, a di-alkyl terephthalate, the method comprising: esterifying two or more of isoheptyl alcohol, 2-ethyl hexanol ("2-EH" or merely, "EH"), isononyl alcohol, isodecyl alcohol, and mixtures thereof with dimethyl terephthalate ("DMT"), optionally, in the presence of at least one solvent. The solvent should ideally dissolve one or more of the reactants, the product, e.g., the terephthalate, and/or the catalyst, or its follow-on products.

In a class of embodiments of the invention, the at least one solvent may be at least one polar solvent, at least one non-polar solvent, and mixtures thereof. The dielectric constant of the solvent provides in general a measure of a solvent's polarity. As used herein, "polar solvent" shall refer to a solvent or solvent mixtures that consists essentially of molecules that generally have a dielectric constant of 15 or more. Conversely, as used herein, "non-polar solvent" shall refer to a solvent or solvent mixtures that consists essentially of molecules that generally have a dielectric constant of less than 15.

The solvent may comprise methanol, dimethylformamide, dimethylsulfoxide, N-methylpyrrolidone, dioxane (1,2-dioxane and/or 1,3-dioxane and/or 1,4-dioxane), a mixture of one or more dioxanes and water, and mixtures thereof.

In any of the embodiments described herein, the production method may comprise an esterification process utilizing a titanate and/or tin catalyst, para-toluene sulfonic acid, and/or a sulfuric acid catalyst as discussed in more detail below.

The production of the terephthalate ester, for example, a di-alkyl terephthalate, may include a process for the preparation of di-(2-ethylhexyl) terephthalate or also known as di-octyl terephthalate (the two terms may be used interchangeably hereinafter along with "DOTP") by the esterification of TPA, PTA, or DMT with 2-EH at a given pressure and temperature in the presence of at least one of methanol, dioxane, a mixture of dioxane and water, and mixtures thereof, to produce the terephthalate. As used herein, TPA and PTA may be referred to collectively as "terephthalic acid". The esterification process may include any suitable method, for example, Fischer-Speier esterification, (Emil Fischer, Arthur Speier (1895), "*Darstellung der Ester*", Chemische Berichte; 28: 3252-3258) and generally refers to the chemical reaction of at least two reactants, typically, alcohols and acids (or their anhydride), in which the reactants form an ester as a product of the chemical reaction. The alcohol may generally be present in an excess as compared to the other reactants and may be a primary or secondary alkyl alcohol. Illustrative examples include without limitation U.S. Pat. Nos. 3,513,078, 3,681,204, 5,324,853, 6,355,817, 7,385,075 and 7,919,649; and EP 2121560A and 2134672A. Esterification may also include what is commonly referred to as transesterification, generally, referring to a process of exchanging the organic group of an ester with the organic group of an alcohol. Illustrative examples include without limitation U.S. Pat. No. 4,929,749 and U.S. Patent Application Publication No. 2008/0194862.

Suitable catalysts that may be used in the esterification process may include acids, such as, for example, sulfuric acid, methanesulfonic acid, or p-toluenesulfonic acid, metals, or metal compounds. Examples of relevant metals include without limitation tin, titanium, and zirconium, which may be used as finely divided metals or in the form of their salts, oxides, or soluble organic compounds. In several embodiments of the invention, the esterification process may include a sulfuric acid catalyst as utilized in the Rhone Poulenc/Melle-Bezons process. Illustrative examples include without limitation U.S. Pat. Nos. 2,787,636, 3,404, 175, 3,431,181, 3,513,078, and 3,681,204.

Other exemplary representatives of metal catalysts employed are tin powder, tin(II) oxide, tin(II) oxalate, titanate esters, such as, for example, tetraisopropyl orthotitanate or tetrabutyl orthotitanate, and zirconium esters such as, for example, tetrabutyl zirconate. In a class of embodiments of the invention, the titanium catalyst may be any titanium compound soluble in the reaction mixture, i.e., soluble in 2-EH and the di-(2-ethylhexyl) terephthalate product. Examples of suitable titanium compounds include titanium tetraalkoxides having the formula $Ti(OR)4$ wherein R is an alkyl group of 1 to 8 carbon atoms.

The catalyst concentration may be varied in wide ranges and in particular may be varied as a function of the type of catalyst. In certain embodiments of the invention, the catalyst concentration may be from 0.005% to 1.0% by mass, based on the reaction mixture, alternatively, from 0.01% to 0.5% by mass, and alternatively, from 0.01% to 0.1% by mass. The catalyst concentration includes all values and subvalues therebetween, including 0.01, 0.05, 0.1, 0.2, 0.3, 0.4, 0.5, 0.6, 0.7, 0.8 and 0.9% by mass. The reaction mixture may be defined as the reactants, product, and any solvent(s) used in the reaction vessel.

In an embodiment of the invention, esterification may be performed in a batch reactor, a continuous flow reactor, such as a distillation column and/or tower, or a cascade of stirred tank reactors with an organic titanate catalyst. Molten or solid reactants may be contacted with "fresh" and/or recycled 2-EH, optionally, with a solvent, and mixed to produce a reaction mixture. As used herein, "fresh" shall refer to a reactant that has never been used in the chemical process/method as claimed. As used herein, "recycled" shall refer to a reactant that has been used at least once in the chemical process/method as claimed. The reaction mixture may then be contacted with the catalyst to produce the terephthalate. The reaction water may be removed by boiling the 2-EH, condensing the water/2-EH mixture, and separating them, followed by refluxing the 2-EH back to the reactor. The product obtained is an ester with low acidity and may undergo further finishing steps described in more detail below.

In another embodiment of the invention, esterification may be performed in a batch or continuous process with an acid catalyst. Molten or solid reactants may be contacted with "fresh" and/or recycled 2-EH, optionally, with a solvent. The reaction mixture may then be contacted with the catalyst and one or more alcohols, and optionally, solvent, to produce the reaction product including the terephthalate esters. The reaction product including unreacted mixture components and byproducts may then be fed to the top of a distillation column. Accordingly, the reaction product will flow downward and it will be stripped with a countercurrent vapor flow with a carrier, such as, for example, hexane. At the top of the column, a mixture of the carrier, the solvent if applied and the reaction water exits the column, while at the bottom of the column the terephthalate, excess alcohol, some carrier, some solvent and the catalyst exit through the bottom of the column and may undergo further finishing steps described in more detail below.

In yet another embodiment of the invention, DOTP may be prepared with molten DMT having a melting point of 142° C. DMT has a much lower melting point than TPA or PTA (≥300° C.), but a higher melting point than phthalic anhydride (131° C.), a commonly accepted material to produce ortho-phthalate esters. The melting point differences provide some advantages of using DMT to produce the para-phthalate or terephthalate. For example, DMT has a higher conversion rate to DOTP than phthalic anhydride to di-octyl phthalate. Equipment designed for the use of phthalic anhydride may also be used for DMT. Additionally, replacing the water in the reaction mixture with methanol may create other efficiencies. In particular, using a partial condenser in the reactor overhead system, the methanol may be separated as vapor from the 2-EH which may be refluxed back to the reactor and by applying a reflux column dissolved methanol is further removed from the 2-EH. The methanol may then be re-purposed, for example, to be used as fuel. Thus, not only can methanol be re-purposed from the process but this embodiment of the invention avoids problems associated with water as it tends to exhibit azeotropic properties with certain reactants which makes separation difficult and requires additional equipment.

For example, FIG. 1 is a schematic representation of an example of a reactor (1) with an overhead system (2) comprising of a fractionation column (3) and of a partial condenser (4). In the reactor, DMT and 2-EH are converted in the presence of a catalyst into DOTP and methanol. By heating the reactor contents, methanol and 2-EH are vaporized and shift the reaction equilibrium towards the DOTP product by the removal of the methanol product. Fractionation of methanol and the alcohol reactant is necessary as these components are very well miscible unlike the alcohol reactant and water. The vapor stream (5) enters the bottom of the fractionation column (3) in which the methanol vapor is purified by a reflux liquid (6) (e.g., 2-EH), which is returned to the reactor (1). The fractionation column has internal components that may be, for example, trays, loose packing, structured packing, or the like. The number of separation stages may be from 1-10, alternatively, from 2-9, alternatively, from 2-7, and alternatively, from 2-5. The vapors leaving the fractionation column (3) enter a partial condenser (4) to condense remaining traces of 2-EH and the cleaned methanol vapor stream (7) may be condensed for recovery or used as a fuel. The partial condenser (4) is operated with a cooling liquid that enters the condenser at the top (8) and leaves it at the bottom (9). The separation between the methanol and the $C_6$-$C_{13}$ alcohol feed may be optimized by controlling the temperature of the cooling liquid, for example, from 30° C. and 80° C., and the operating pressure of the overhead system, for example, from 2.0 barg and 0.1 bara. Suitable cooling liquids may be without limitation water, glycol, heat transfer oils, and mixtures thereof.

In any embodiment, the method comprises a reaction temperature of from 150°-270° C. and a reaction pressure of from 10 to 500 kPa (0.01 bar absolute (bara) to 4 bar gauge (barg)). In yet other embodiments, the method comprises a reaction temperature of from 80° to 170° C. and a reaction pressure of from 10 to 500 kPa (0.01 bar absolute (bara) to 4 bar gauge (barg)).

In a particular embodiment of the invention, the invention provides for a process for the preparation of di-(2-ethylhexyl) terephthalate that comprises contacting DMT with 2-EH in the presence of a titanium catalyst in a reaction zone wherein the total pressure may be maintained at 10 to 400 kPa (0.1 to 4 bar gauge (barg)), the temperature may be maintained from 150° C.-270° C., the 2-EH:DMT mole ratio may be maintained at 2:1 to 2.5:1, and an inert gas may be passed through the reaction mixture in the reaction zone.

In a class of embodiments of the invention, the reaction temperatures may be for acid catalysts from 80° C.-200° C., and for metal catalysts from 160° C.-270° C., alternatively, from 180° C.-250° C. The temperature includes all values and subvalues therebetween, including 80, 90, 100, 110, 120, 130, 140, 150, 160, 170, 180, 190, 200, 210, 220, 230, 240, 250 and 260° C. However, in general, the optimum temperatures for carrying out the esterification process primarily depend on the catalyst, the reactants, the composition of the reaction mixture, on the progress of the reaction, and on the catalyst concentration. The optimum temperatures for each individual case can be readily determined by means of simple tests. Through the use of higher temperatures it is possible to increase the reaction rate, although mitigating side reactions, such as elimination of water from alcohols or formation of byproducts, may pose challenges with higher temperatures.

The desired reaction temperature or the desired temperature range may be controlled by adapting the pressure in the reaction vessel. In a class of embodiments, the reaction may be carried out under reduced pressure in the case of higher-boiling alcohols and the reaction may be carried out at overpressure in the case of lower-boiling alcohols. Thus, the esterification process may be carried out under pressures from 0-1 bar, or from 1 to 10 bar, alternatively, 2 to 8 bar.

The inert gas may be nitrogen and is typically used given that it is readily available. The inert gas typically is fed below the surface of the reaction mixture by means of a conventional conduit or via a gas sparging device. While the inert gas may be fed intermittently or discontinuously, it is preferably fed continuously at the commencement of the esterification reaction in many embodiments of the invention. The amount of gas passed through the reaction mixture may vary significantly but typically is in the range of from 0.5 to 5 volumes of gas per volume of reaction mixture per hour.

Processes of the invention may be carried out in a batch, semi-continuous, or continuous mode. In an embodiment of the invention, operating in batch mode, an agitated pressure vessel may be charged with DMT, 2-EH, and a catalyst, heated, and pressurized and the esterification is carried out while passing an inert gas through the reaction mixture. 2-EH and a solvent employed may be removed as a mixture and EH may be fed and recycled to the reaction vessel over the course of the process. At the conclusion of the process, the di-(2-ethylhexyl) terephthalate product is recovered from the vessel and purified according to conventional procedures.

In other embodiments of the invention, continuous operation may involve continuously or intermittently feeding TPA, PTA and/or DMT, 2-EH, and a catalyst to a vessel and continuously or intermittently removing 2-EH, solvent, and product mixture from the vessel maintained at a predetermined temperature, pressure, and liquid level. At the conclusion of the process, the di-(2-ethylhexyl) terephthalate product is recovered from the vessel and purified according to conventional procedures.

In yet another embodiment, the process may be practiced in a continuous mode by adding the DMT to a suitable reaction vessel by means of a grinder or other mechanical device to reduce the particle size to below 50 micron, a screw feeder, and the 2-EH/solvent/catalyst as a pump-fed mixture to a stirred, optionally, pressurized reaction vessel equipped with a reflux condenser/decanter combination such that the reaction by-products methanol and/or water may be removed and the unreacted EH returned to the vessel. At the conclusion of the process, the di-(2-ethylhexyl) terephthalate product is recovered from the vessel and purified according to conventional procedures.

The esterification may be performed in the presence of a solvent, which may be an aromatic, a hydrocarbon, non-polar or polar solvent. Suitable examples are but not limited to benzene, toluene, xylenes, pentane, hexane, heptane, tetrahydrofuran, dioxane (1,2-dioxane and/or 1,3-dioxane and/or 1,4-dioxane), butanol, pentanol, dimethyl formamide (DMF), N-methylpyrrolidone, pyridine, acetone, dimethyl sulfoxide, methyl ethylketone, methyl isobutylketone, and mixtures thereof.

Conventional procedures include treating the reaction mixture to further refine and concentrate the desired end product. The reaction mixture after esterification or effluent may include ester product(s), any of the reactants including 2-EH, catalyst or its follow-on products, solvents, and, often byproducts. Finishing steps may include any combination of the following: separating off the excess alcohol and any low boilers, neutralizing the acids present, caustic or water wash of the neutralized products, performing steam distillation, converting the catalyst into a readily filterable residue, addition of filter aid and/or solid treating agents, separating off the solids, and, where appropriate, drying. The sequence of these steps may differ according to the specific method employed.

In another embodiment of the invention, the reaction mixture after the esterification process or effluent may be further treated by filtering out unreacted reactants for recycle. The product may also be neutralized with a wash of water or wash of an aqueous solution, for example, an aqueous sodium carbonate and/or an aqueous sodium hydroxide solution, and, filtered with an adsorbent, for example, clay, perlite, kieselguhr, charcoal, activated carbon, etc. The product may also be steam stripped. The stripped product may further be treated with the same or different adsorbent and then filtered through a filter aid to yield the final product.

In yet another embodiment of the invention, the reaction mixture after the esterification process or effluent may first be neutralized with an aqueous solution, for example, an aqueous sodium carbonate and/or an aqueous sodium hydroxide solution, followed by separation of the organic and non-organic (water) phases. Further refinement of the terephthalate may proceed with water washing, steam stripping (optionally, under vacuum conditions), and drying.

Various alternative finishing schemes exist, such as, for example, without a washing step or filtration after neutralization. The finishing process may also proceed continuously, semi-continuously, or in a batch mode.

It is to be understood that while the invention has been described in conjunction with the specific embodiments thereof, the foregoing description is intended to illustrate and not limit the scope of the invention. Other aspects, advantages and modifications will be apparent to those skilled in the art to which the invention pertains.

Therefore, the following examples are put forth so as to provide those skilled in the art with a complete disclosure and description and are not intended to limit the scope of that which the inventors regard as their invention.

Example 1

A 45 m$^3$ batch reactor equipped with a mixer, heating coil, a fractionation column and partial condenser, as shown in FIG. 1, will be used for the batch trans-esterification of DMT. Fresh preheated 2-EH of 130° C. (13,020 kg) and recycled 2-EH (3255 kg) will be added to this reactor and stripped with nitrogen for removal of dissolved gases. Subsequently, molten DMT (9700 kg) will be added, while stirring and heating to 150° C., followed by the addition of tetra-isopropyl titanate (20 kg). Upon addition of the catalyst, evolution of methanol will be expected to take place. The reactor will be kept at above atmospheric pressure (1.5 barg) with a cooling fluid temperature of 70° C. in the condenser. The temperature of the reactor will be increased to 210-220° C. A constant evolution rate of methanol will be achieved by gradually reducing the reactor operating pressure from 1.5 barg to vacuum (0.3 bara). Simultaneously, the temperature of the cooling liquid in the condenser will be reduced to 40° C. The reaction will be expected to be complete when methanol is no longer recovered from the reactor which typically occurs after 3 hr of reaction with >99.8% conversion to yield an expected 19481 kg DOTP. The methanol vapors leaving reactor overhead condenser will be condensed and collected in a vessel for further use or disposal. Alternatively, the vapors may be directly injected into a furnace for use as combustion fuel.

The reaction product is discharged into another vessel, optionally cooled to 120° C. for catalyst decomposition and neutralization. 1 wt % of an aqueous (5 wt %) sodium carbonate solution is added based on the total ester weight and allowed to mix for 15 minutes. Pressure is reduced to vacuum to vaporize the water. The mixture is subsequently stripped under vacuum with steam at 160° C. to remove the excess alcohol. Vacuum is broken with nitrogen. After discharging the product is further purified by filtration over a pre-coated filter and in the presence of perlite filter aid.

Example 2

A 45 m$^3$ batch reactor equipped with a mixer, heating coil, a fractionation column and partial condenser, as shown in FIG. 1, will be used for the batch trans-esterification of DMT. Fresh preheated 2-EH of 110° C. (12,535 kg) and recycled 2-EH (3255 kg) will be added to this reactor and stripped with nitrogen for removal of dissolved gases. Subsequently, molten DMT (9700 kg) will be added, while stirring and heating to 130° C. In a second mixing vessel, 48.5 kg 98% sulfuric acid will be mixed into 484 kg 2-EH at ambient temperature and added to the reactor. Upon addition of the catalyst, evolution of methanol will be expected to take place. The reactor will be kept slightly above atmospheric pressure (1.1 barg) with a cooling fluid temperature of 60° C. in the condenser. The temperature of the reactor will be increased to 140° C. A constant evolution rate of methanol will be achieved by gradually reducing the reactor operating pressure from 1.1 barg to vacuum (0.3 bara). Simultaneously, the temperature of the cooling liquid in the condenser will be reduced to 40° C. The reaction will be complete when methanol is no longer recovered from the reactor which typically occurs after 3 hr of reaction with 98% conversion to yield an expected 19130 kg DOTP. The methanol vapors leaving reactor overhead condenser will be condensed and collected in a vessel for further use or disposal. Alternatively, the vapors may be directly injected into a furnace for use as combustion fuel.

What is claimed is:

1. A method to produce a terephthalate ester, the method comprising: esterifying at least one $C_6$-$C_{13}$ alcohol with di methyl terephthalate (DMT) in the presence of a catalyst to produce the terephthalate ester and methanol in a reactor; wherein the terephthalate ester is recovered and at least a portion of the $C_6$-$C_{13}$ alcohol is recovered by fractionation using at least one distillation column and the partial condensation of the methanol is carried out in a partial condenser, wherein the partial condensation of the methanol is operated with a cooling liquid that enters the partial condenser; and wherein the DMT is fed into the reactor as molten DMT.

2. The method of claim 1, wherein the catalyst is an organic titanate catalyst.

3. The method of claim 1, wherein the catalyst comprises a compound selected from the group consisting of tin powder, tin (II) oxide, tin (II) oxalate, titanate esters, titanium tetraalkoxides, zirconium esters, and mixtures thereof.

4. The method of claim 1, wherein the catalyst is an acid catalyst.

5. The method of claim 4, wherein the acid catalyst comprises an acid selected from the group consisting of sulfuric acid, sulfonic acid, methanesulfonic acid, p-toluenesulfonic, and mixtures thereof.

6. The method of claim 1, wherein the at least one $C_6$-$C_{13}$ alcohol is selected from $C_8$-$C_{10}$ alcohols and mixtures thereof.

7. The method of claim 1, wherein the at least one $C_6$-$C_{13}$ alcohol is 2-ethyl hexanol (2-EH).

8. The method of claim 7, wherein the 2-EH comprises fresh 2-EH and recycled 2-EH.

9. The method of claim 1, wherein the terephthalate ester is di-alkyl terephthalate.

10. The method of claim 1, wherein the terephthalate ester is di-octyl terephthalate (DOTP).

11. The method of claim 1, wherein the method is a batch method.

12. The method of claim 1, wherein the method utilizes a reactor system selected from the group consisting of a batch reactor, a continuous flow reactor, a cascade of stirred tank reactors, and any combination thereof.

13. The method of claim 1, wherein the method further comprises esterifying in the presence of at least one solvent.

14. The method of claim 7, wherein the 2-EH, following the production of the terephthalate ester, is at least partially refluxed back to esterification process.

15. The method of claim 14, wherein the methanol, following the production of the terephthalate ester, is at least partially separated from the 2-EH and at least partially recovered.

16. The method of claim 1, wherein the method comprises an esterification reaction temperature of from 150° C.-270° C. and a reaction pressure of from 10 to 500 kPa.

17. The method of claim 1, wherein the method comprises an esterification reaction temperature of from 80° C.-170° C. and a reaction pressure of from 10 to 500 kPa.

18. The method of claim 1, wherein the cooling fluid is maintained at a temperature of from 30° C. to 80° C.

* * * * *